US010679018B1

(12) United States Patent
Narayanan et al.

(10) Patent No.: US 10,679,018 B1
(45) Date of Patent: Jun. 9, 2020

(54) MAGNETIC TRACKING FOR MEDICINE MANAGEMENT

(71) Applicant: INTERNATIONAL BUSINESS MACHINES CORPORATION, Armonk, NY (US)

(72) Inventors: Rajeev Narayanan, Briarcliff Manor, NY (US); Bing Dang, Chappaqua, NY (US); Bo Wen, New York, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 0 days.

(21) Appl. No.: 16/268,425

(22) Filed: Feb. 5, 2019

(51) Int. Cl.
*G06K 7/08* (2006.01)
*G06K 19/06* (2006.01)

(52) U.S. Cl.
CPC ....... *G06K 7/087* (2013.01); *G06K 19/06187* (2013.01)

(58) Field of Classification Search
CPC .......................... G06K 7/087; G06K 19/06187
USPC .......................................................... 235/449
See application file for complete search history.

(56) References Cited

U.S. PATENT DOCUMENTS

| | | | |
|---|---|---|---|
| 4,674,480 A | 6/1987 | Lemelson | |
| 5,310,060 A | 5/1994 | Bitner et al. | |
| 5,511,665 A | 4/1996 | Dressel et al. | |
| 7,008,668 B2 | 3/2006 | Hogan et al. | |
| 7,370,797 B1 * | 5/2008 | Sullivan | G06K 17/00 |
| | | | 235/462.01 |
| 8,436,291 B2 * | 5/2013 | Owen | G01V 8/20 |
| | | | 250/222.1 |
| 9,047,746 B1 | 6/2015 | Euliano | |
| 9,050,256 B2 | 6/2015 | Hartwig | |
| 9,235,683 B2 | 1/2016 | Robertson | |
| 10,060,860 B2 | 8/2018 | Popp | |
| 10,165,988 B2 | 1/2019 | Hartwig et al. | |
| 10,469,723 B2 | 11/2019 | Pincenti et al. | |
| 2003/0023150 A1 | 1/2003 | Yokoi | |
| 2004/0138558 A1 | 7/2004 | Dunki-Jacobs | |
| 2005/0043634 A1 | 2/2005 | Yokoi | |
| 2005/0049488 A1 | 3/2005 | Homan | |

(Continued)

OTHER PUBLICATIONS

List of IBM Patents or Applications Treated as Related.

*Primary Examiner* — Daniel A Hess
*Assistant Examiner* — David Tardif
(74) *Attorney, Agent, or Firm* — Intelletek Law Group, PLLC; Gabriel Daniel, Esq.

(57) ABSTRACT

A magnetic tracking apparatus, method, system and computer program product for magnetically encoding pills are provided. A pill feeder includes a first valve controlling an opening of the pill feeder. A chamber is arranged in communication with an outlet of the pill feeder, and a second valve when closed retains the pill within the chamber, and when open communicates with a passageway for the pill to exit the chamber. A microcontroller is configured to control operation of the first valve and the second valve. A magnetic nano-particle applicator deposits bio-compatible nano-magnetic particles in a magnetic pattern onto a surface of the pill within the chamber. A system for detection of the pill includes a wearable patch or article including a magnetic reader to read the magnetic pattern on a coated pill when consumed by the patient.

20 Claims, 9 Drawing Sheets

(56) References Cited

U.S. PATENT DOCUMENTS

| | | |
|---|---|---|
| 2005/0131281 A1 | 6/2005 | Ayer |
| 2005/0163866 A1 | 7/2005 | Alex |
| 2005/0216231 A1 | 9/2005 | Aoki |
| 2006/0152309 A1* | 7/2006 | Mintchev ........... A61B 1/00158 335/58 |
| 2007/0002038 A1 | 1/2007 | Suzuki |
| 2007/0008113 A1 | 1/2007 | Spoonhower |
| 2007/0049818 A1 | 3/2007 | Hirakawa et al. |
| 2007/0123772 A1 | 5/2007 | Euliano |
| 2007/0237719 A1 | 10/2007 | Jones |
| 2008/0069878 A1 | 3/2008 | Venkatesh et al. |
| 2008/0175898 A1 | 7/2008 | Jones |
| 2009/0009332 A1 | 1/2009 | Nunez et al. |
| 2009/0171146 A1 | 7/2009 | Fujita |
| 2009/0216082 A1* | 8/2009 | Rabinovitz ........ A61K 49/1818 600/118 |
| 2009/0318762 A1 | 12/2009 | Segawa |
| 2010/0222670 A1 | 9/2010 | Demierre |
| 2010/0322859 A1 | 12/2010 | Jones |
| 2011/0101914 A1* | 5/2011 | Niessen ............... H01M 10/425 320/107 |
| 2011/0244040 A1 | 10/2011 | Ono et al. |
| 2012/0059389 A1* | 3/2012 | Larson ................... A61N 1/056 606/129 |
| 2013/0012758 A1 | 1/2013 | Chen |
| 2013/0312619 A1 | 11/2013 | Spiegel |
| 2014/0141085 A1 | 5/2014 | Barashkov |
| 2014/0163664 A1* | 6/2014 | Goldsmith ....... A61B 17/00491 623/1.11 |
| 2014/0345468 A1 | 11/2014 | Talon |
| 2015/0065801 A1 | 3/2015 | Chiba |
| 2016/0287058 A1* | 10/2016 | Ye .......................... A61B 1/126 |
| 2016/0379024 A1 | 12/2016 | Tippery |
| 2017/0181661 A1 | 6/2017 | Chiba |
| 2017/0354573 A1* | 12/2017 | Lee ...................... A61J 7/0418 |
| 2018/0125390 A1 | 5/2018 | Bouchoucha |

* cited by examiner

MAGNETIC TRACKING FOR MEDICINE MANAGEMENT

BACKGROUND

Technical Field

The present disclosure generally relates to the tracking of medicines and medication management, and more particularly, to systems and methods of identifying and marking pills for medicine management.

Description of the Related Art

The arrangement of non-toxic magnetic nano-particles (MNPs) on the surface of pills has been provided for medical treatment. For example, a pill coated with MNPs can be steered by a series of magnetic pulses to a specific part of a body where, for example, a tumor may be present. Also, the use of MNPs to coat pills to provide contrast in Magnetic Resonance Imaging (MRI's) has been studied to detect traces of certain medicines.

SUMMARY

According to an embodiment of the present disclosure, a magnetic tracking apparatus includes a pill feeder having an inlet, an outlet, and a first valve configured to control opening and closing of the outlet of the pill feeder. There is a chamber arranged in communication with the outlet of the pill feeder to receive at least one pill. The chamber includes a second valve having a closed position that retains the at least one pill within the chamber, and in an open position communicates with a passageway for the at least one pill to exit the chamber. There is at least one microcontroller and a wireless communication system configured to control operation of the first valve and the second valve. A magnetic nano-particle sprayer is controlled by the at least one microcontroller to spray bio-compatible nano-magnetic particles in a magnetic pattern onto a surface of at least one pill within the chamber.

In one embodiment, the magnetic pattern includes at least one or more of a barcode, a hologram, a U.S. Food and Drug Administration (FDA) imprint code, a Quick Response (QR) code, a National Drug Code (NDC) number, or any other unique signature.

According to an embodiment of the present disclosure, a method for identifying and tracking pills includes reading, by an input reader, information associated with at least one pill to be tracked. Under control of at least one microcontroller and a wireless communication system operatively coupled thereto, a first valve configured to control an opening and a closing of an outlet of a pill feeder is opened. Under control of the at least one microcontroller, a magnetic pattern of nano-particles is deposited onto a surface of the at least one pill within a chamber arranged in communication with the outlet of the pill feeder in which the chamber includes a second valve having a closed position that retains the at least one pill within the chamber, and in an open position communicates with a passageway for the at least one pill to exit the chamber. A pill collector receives the at least one pill having the magnetic pattern deposited thereon.

In one embodiment, an operation of depositing magnetic nano-particles onto the surface of the at least one pill is performed by a sprayer.

In one embodiment, an operation of depositing magnetic nano-particles onto the surface of the at least one pill is performed by an inkjet printer.

In one embodiment, an operation of depositing magnetic nano-particles onto the surface of the at least one pill is performed by stencil printing.

In one embodiment, the reading of information by the input reader includes reading a label associated with the at least one pill to be tracked.

In one embodiment, the reading of information by the input reader includes reading an imprint code on the at least one pill to be tracked.

The techniques described herein may be implemented in a number of ways. Example implementations are provided below with reference to the following figures.

BRIEF DESCRIPTION OF THE DRAWINGS

The drawings are of illustrative embodiments. They do not illustrate all embodiments. Other embodiments may be used in addition or instead. Details that may be apparent or unnecessary may be omitted to save space or for more effective illustration. Some embodiments may be practiced with additional components or steps and/or without all of the components or steps that are illustrated. When the same numeral appears in different drawings, it refers to the same or like components or steps.

DETAILED DESCRIPTION

Overview

In the following detailed description, numerous specific details are set forth by way of examples in order to provide a thorough understanding of the relevant teachings. However, it should be apparent that the present teachings may be practiced without such details. In other instances, well-known methods, procedures, components, and/or circuitry have been described at a relatively high-level, without detail, in order to avoid unnecessarily obscuring aspects of the present teachings.

It is to be understood that the term "pill", as used in this disclosure, may broadly refer to any enclosed system of delivery (typically oral) of chemical compounds to a patient, including but not limited to at least a tablet, a capsule, a caplet, a soft gel, etc. The term pill, as used in this disclosure, may represent prescription and/or over-the-counter (OTC) medication, but the term is not limited to such a definition. For example, the pill may include enzymes, supplements, etc., or any other substance in pill form that is desired to be tracked.

The present disclosure generally relates to systems and methods of identifying and marking pills for medicine management. By providing a magnetic pattern of nano-particles on the surface of the pill, there is an improvement in the tracking of patients taking their medication as prescribed, and a resultant improvement in the overall health of patients at a reduced cost of treatment. A computer program product that is executed by the processor of a device including but not limited to a smart device provides additional improvements and advantages in medicine management.

Example Architecture of a Magnetic Tracking Apparatus

Figure 1A:
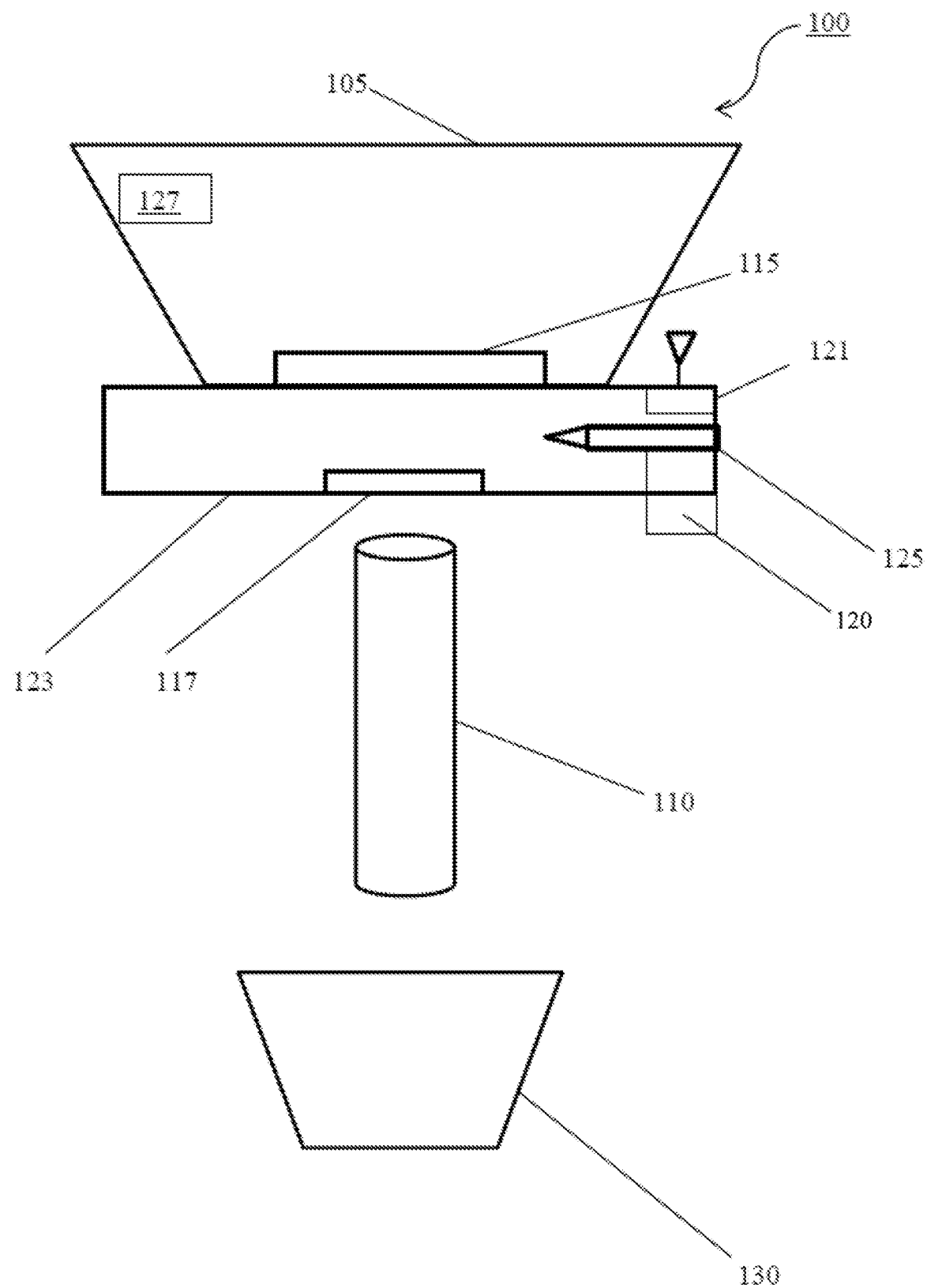
FIG. 1A shows a magnetic tracking apparatus, consistent with an illustrative embodiment of the present disclosure.

To better understand the features of the present disclosure, it may be helpful to discuss architectures of the magnetic tracking apparatus. FIG. 1A is an illustration of a magnetic tracking apparatus 100, which according to an embodiment of the present disclosure, may include a pill feeder 105 having an inlet and an outlet, and a pill conduit 110 arranged at the outlet of the pill feeder. A first valve 115 is configured to control the opening and closing of a passageway formed by at least the outlet of the pill feeder 105 and the pill conduit 110.

A microcontroller 120 is configured to control opening and closing of the first valve 115. A magnetic nano-particle applicator, which in this embodiment is shown by a sprayer 125 that is configured to spray bio-compatible nano-magnetic particles into a chamber 123 arranged between the first valve 115 and the pill conduit 110 to spray a magnetic pattern onto a surface of at least one pill within the chamber 123. It is to be understood that the magnetic nano-particle applicator may be embodied in various forms, for example, an inkjet printer, or a stencil printer, configured to deposit the magnetic nano-particles onto the surface of the pill.

The chamber 123 includes a second valve 117, under control of the microcontroller 120. The second valve 117, for example, may be closed for a predetermined time period (e.g. two to three seconds) so that a pill that has entered the chamber via, for example, the pill feeder 105, can be included within the chamber so that the magnetic nano-particle sprayer 125 may spray a magnetic pattern on the surface of the pill for subsequent identification. The microcontroller 120 may be configured to monitor the conditions of the first valve, second valve, magnetic nano-particle applicator by a wireless communication system 121 operatively coupled to the microcontroller 120. For example, the wireless communication system a transceiver may send commands and receive status information from sensors configured to monitor the various components of the magnetic tracking apparatus. The wireless communication system 121 may be configured for communication with a smart device, such as a smartphone or smart watch.

With continued reference to FIG. 1A, a pill collector 130 may be substantially aligned with the pill conduit to receive the pill having the bio-compatible nano-magnetic pattern on at least a portion of its surface. The pill collector 130 is optional, because in some embodiments of the present disclosure, the pill collector 130 may be a pill bottle used to dispense drugs to a patient. The pill collector 130 may be placed in alignment with the pill conduit 110. Alternatively, or in addition thereto, an optical sensor (not shown) may be used to count the pills as they enter the pill collector 130. In addition, the sensor used to count the pills may be operatively coupled via a buffer to a display that displays the number of pills in the pill collector 130.

In an embodiment of the present disclosure, the magnetic tracking apparatus may include an input reader 127. It will be understood that the input reader 127, while shown in FIG. 1A as being arranged in the pill feeder 105, may be positioned differently than shown, and in some embodiments of the present disclosure, may be external to the pill feeder 105. The input reader 127 may be realized as a handheld device with a scanner.

The input reader 127 may be operatively coupled to the microcontroller 120 via wireless communication (e.g., Digital Enhanced Cordless Telecommunications (DECT), Near Field Communication (NFC), ZigBee, WiFi, and Bluetooth, etc.), and may provide information scanned by the input reader 127 to the microcontroller 120.

In another embodiment of the present disclosure, the input reader 127 may be a scanner, such as a bar code scanner or a Quick Response (QR) code scanner that is external to the magnetic tracking apparatus. The input reader 127 may read the bar code, QR code, or the National Drug Code (NDC) number imprinted on the label of a container bottle of the medication. The NDC number is currently a unique 10-digit, 3-segment number. The NDC number is a universal product identifier for human drugs in the United States, and the NDC number is present on all non-prescription over-the-counter (OTC) and prescription medication packages and inserts in the US.

The label may include a code imprinted with magnetic ink used for magnetic ink character recognition (MICR). Such a code may be used to identify the type of pills that are about to be placed, or already placed in the pill feeder 105. The bar code scanner or QR code scanner may be a handheld device, including but not limited to a dedicated device, or may be a module of a smartphone. For example, the smartphone may scan the code on the label, and the smartphone may include an app that is used to communicate with a transceiver of the magnetic tracking apparatus that is operatively coupled to the microcontroller 120.

In addition, the QR code may be a dynamic QR code that provides a Uniform Resource Locator (URL). Alternatively, the smartphone may read the NDC number from the label, or a link to a server that includes information about the magnetic coding.

Alternatively, or in addition to the input reader 127 identifying the pill based on a code obtained by scanning the label, there may be magnetic pattern information included on the label that is read by the input reader. For example, this information may be a code that is transmitted to a transceiver that is operatively coupled to the microcontroller 120 to select a pattern of magnetically sprayed nano-particles.

In an embodiment of the present disclosure, the input reader 127 may be configured to scan an actual pill, for example, a pill in the pill feeder 105. The input reader may be configured to scan at least a U.S. Food and Drug Administration (FDA) imprint code on one or more pills in the pill feeder 105. All approved prescription and over-the-counter solid, oral dosage medications in the U.S. are required by the Food and Drug Administration (FDA) to have a unique imprint approved by the FDA (see generally 27 CFR 206.10), including biological drug products and homeopathic drug products, unless exempted by the FDA (21 CFR 206.7). In this embodiment, the input reader 127 may include an optical sensor (not shown), (for example, a charge-coupled device CCD or a CMOS sensor), that may scan the pill and transmit the image data to a memory operatively coupled to the microcontroller 120. The imprint code scanned by the input reader 127 may be provided to the microcontroller 120 for identification. Alternatively, a server in communication with the input reader may identify a type of medication based on the scanned imprint code and provide the microcontroller 120 with magnetic pattern information.

In one embodiment, as jurisdictions outside of the United States may use different types of visual marking to identify prescription and over-the-counter (OTC) medications in place of an imprint code, the pill tracking apparatus may be configured for visual identification of such markings.

Alternatively, or in addition to the scanning of pills for the FDA imprint code, other physical attributes of the pill (e.g. shape, size, color, weight) may be used to identify the type of pill arranged in the pill feeder 105. Moreover, the pill may be scanned prior to being arranged in the pill feeder 105.

In some embodiments of the present disclosure, there may be more than the one microcontroller 120 shown in FIG. 1A to control various operations of the magnetic tracking apparatus. Alternatively, for example, there may be a microprocessor (not shown) that is operatively coupled to the microcontroller 120. In addition, the microcontroller 120 may be configured to control the magnetic nano-particle sprayer to spray a magnetic pattern onto at least a portion of the pill based on the imprint code that was read by the input reader 127.

In some embodiments of the present disclosure, the input reader 127 may communicate with a server via a transceiver and provide the scanned information of the pill. In turn, the server may provide a wireless transceiver operatively coupled to the microcontroller 120 with information regarding a magnetic pattern to be sprayed on at least a portion of the surface of a pill by the magnetic nano-particle sprayer 125.

In another embodiment of the present disclosure, the operation of scanning the pills for an imprint code (or size, shape, color, etc.,) may be performed for the first pill or a few pills, and in the case of, for example, a dispensing pharmacy, the remaining pills of the same type (e.g., when filling a prescription for 30 days or 90 days of the same medication) can be magnetically sprayed with nano-particles without scanning every pill that is placed into the pill feeder 105.

Figure 1B:
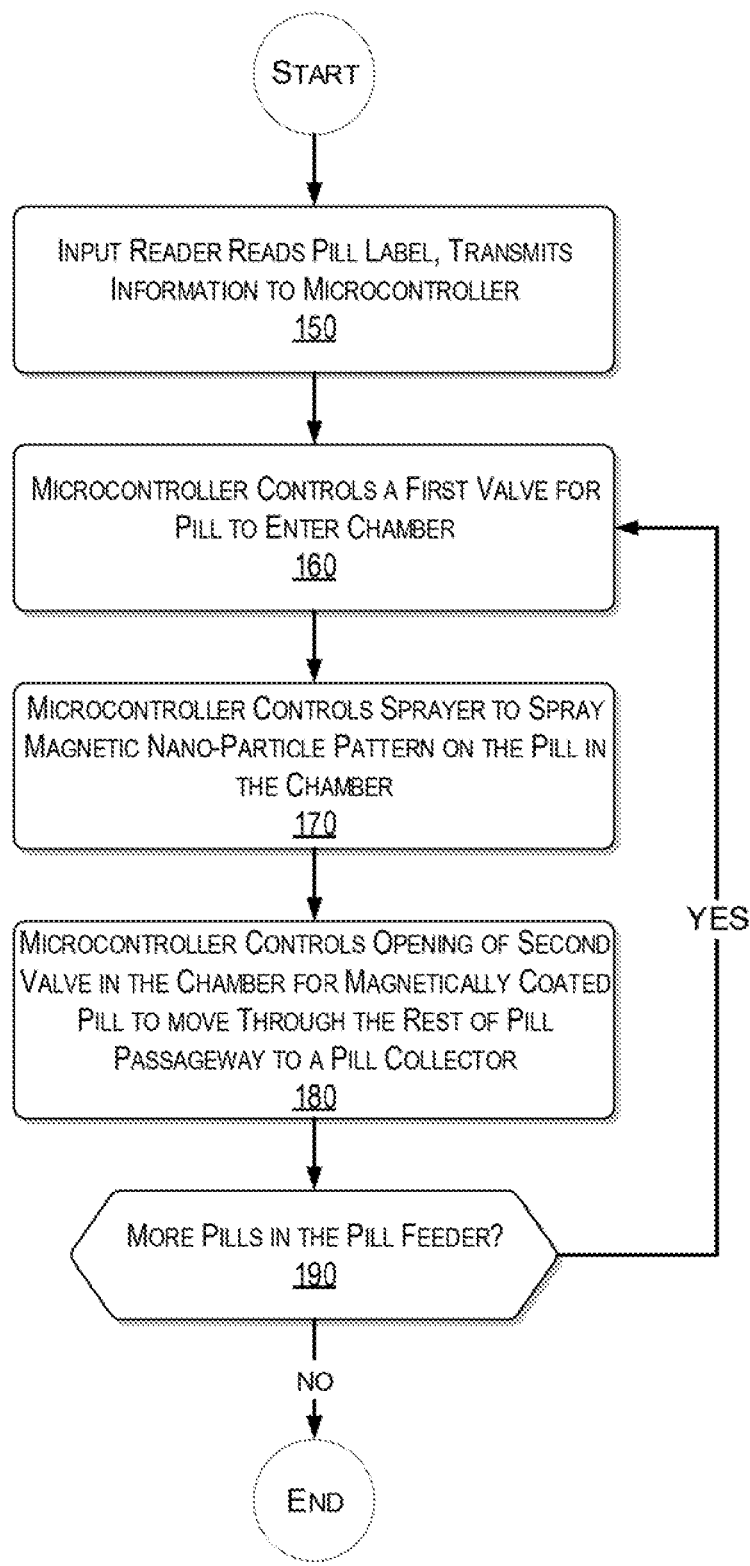
FIG. 1B is a flowchart showing operation of a method for identifying and tracking pills, consistent with an illustrative embodiment of the present disclosure.

FIG. 1B is a flowchart showing operation of a method for identifying and tracking pills, consistent with an illustrative embodiment of the present disclosure. In this embodiment, a magnetic tracking apparatus such as discussed hereinabove with regard to FIG. 1A may be used. However, it is understood that the method to be discussed hereinbelow is not limited to use with the previously-described magnetic tracking apparatus.

At operation 150, the input reader 127 reads a pill label. As discussed hereinabove, this label may be a magnetic label on a bottle of pills stored at a pharmacy, hospital, nursing home, etc., and the label may include information such as a type of medication, a dosage, an NDC number, an imprint code, an expiration date, etc. In addition, this label may be a label created by a local pharmacy, nursing home, etc., that is used by a licensed pharmacist or assistant to fill a prescription. This pill label is read (e.g., scanned) by the input reader.

The pill label, as discussed hereinabove, may be a bar code, QR code, or another type of code that is read by the input reader 127. The input reader 127 may then transmit the label information to the microcontroller 120.

The type of magnetic nano-particles (MNP) used to spray encoding information may include organic, inorganic and organosilicon compounds. The surface of MNPs may be coated by non-toxic organic coatings such as chitosan, dextran and liposomes, as well as inorganic coatings to minimize inflammatory or toxic effects on cell membranes within the body of a patient.

At operation 160, the microcontroller 120 opens a first valve 115 in communication with the pill feeder 105 to permit at least one pill to enter the chamber 123. When the at least one pill enters the chamber, the second valve 117 is closed so that the at least one pill remains within the chamber 123. The second valve 117 may have its opening and closing be controlled by the microcontroller 120.

At operation 170, the microcontroller 120 controls the sprayer 125 to deposit a magnetic pattern on the at least one pill within the chamber 123. The magnetic pattern, as discussed above, may be an imprint code, an NDC number, a bar code, a QR code, a logo, a hologram, an alphanumeric code, or any combination of the aforementioned patterns. In addition, the pharmaceutical manufacturer may determine a magnetic pattern that may be recommended for use. The magnetic pattern may be selected based on the shape and size of the pill, and to facilitate, for example, reading the magnetic pattern on the pill by an external magnetic reader, particularly when consumed by the patient. While operation 170 shows a sprayer 125 that deposits the magnetic pattern of nano-particles onto the pill within the chamber, the inventive concept is not limited to the aforementioned configuration. For example, depositing the magnetic nano-particles onto the surface of the pill may be performed by inkjet printing, or by stencil printing, just to name a few non-limiting examples. The non-toxicity of any materials used to deposit the magnetic nano-particles onto the pill is a consideration in this operation.

At operation 180, the microcontroller 120 opens an outlet (e.g. the second valve 117) so that the pill may exit the chamber 123 and enter a passageway toward the pill collector 130. The passageway may be formed in part by the pill conduit 110. The microcontroller 120 may then close the second valve 117.

At operation 190, if there are more pills in the pill feeder 105, then the microcontroller may open the first valve 115 so that another pill may enter the chamber 123 to have a magnetic pattern sprayed thereon. The input reader 127, for example, or a sensor in the pill feeder 105, may sense whether there are additional pills in the pill feeder 105. If there are no more pills in the feeder the method ends. The pills in the pill collector 130, which have been encoded with the magnetic pattern, may then be distributed to a patient, or removed from the pill collector 130 and placed in a pill bottle or container. In the case where the pill collector 130 is a pill bottle or container, a cap and/or a seal may be placed on the pill bottle.

System for Medication Detection

Figure 2A:
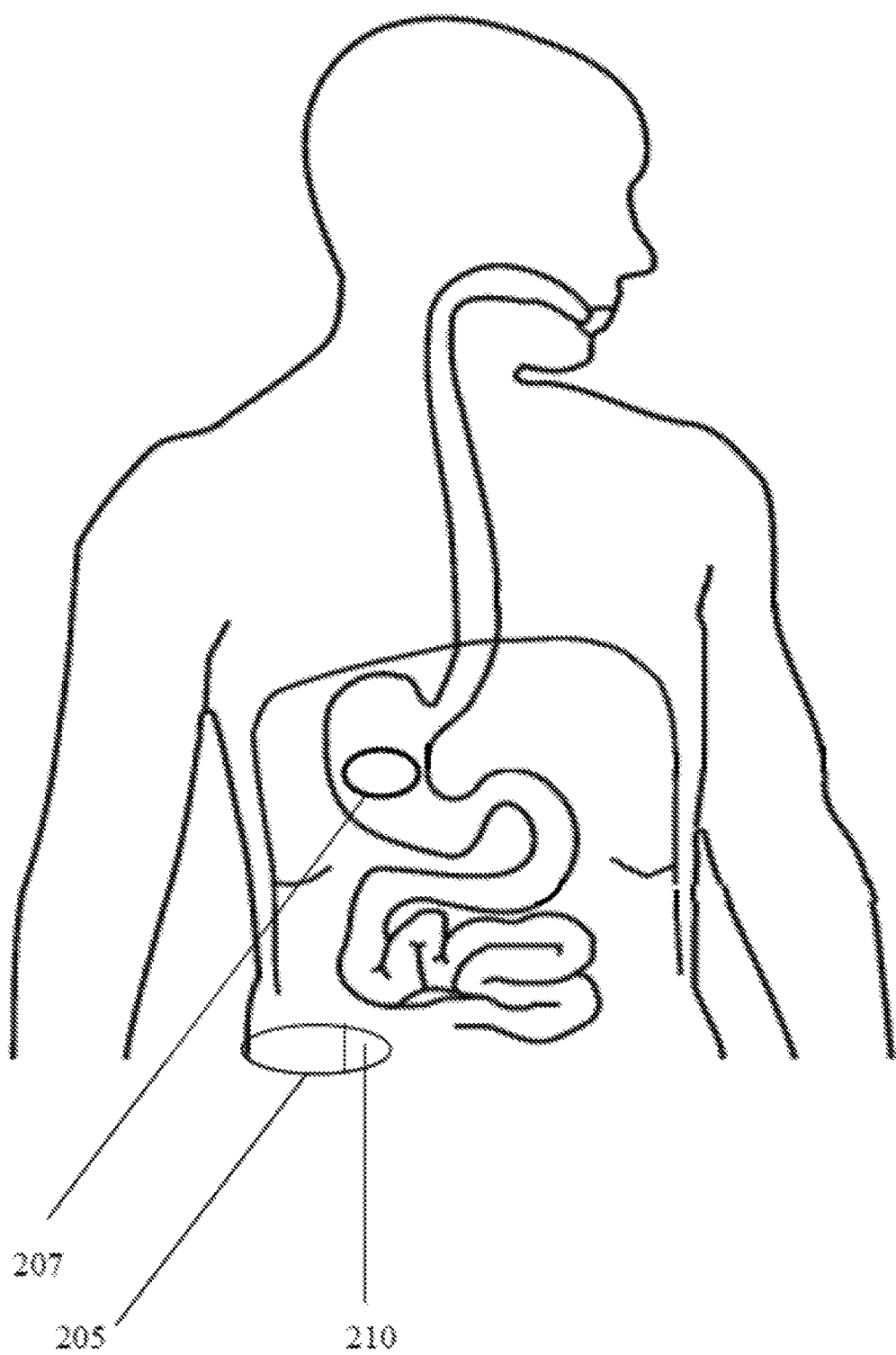
FIG. 2A is an illustration of a patient wearing a magnetic reader in a system for medication detection, consistent with an illustrative embodiment of the present disclosure.

Referring now to FIG. 2A, in another embodiment of the present disclosure, a system for medication detection may include a wearable device 200 to detect whether a pill having a pattern of bio-compatible nano-magnetic particles on its surface has been consumed by a person (or other living being). In an embodiment, the wearable device 200 may detect whether the pill is within the stomach of a person. The pill may have a magnetic pattern arranged on at least a portion of its outer surface by a magnetic tracking apparatus 100 as shown in FIG. 1 and described above.

As shown in FIG. 2A, the wearable device 200 includes a magnetic reader 205 configured to perform a read operation to detect whether a pattern of bio-compatible nano-magnetic particles is detected in the stomach of a person. In addition, a wireless transceiver 210 is operatively coupled to the magnetic reader 205 (see FIG. 2B), and the wireless transceiver 210 may be configured to transmit information from the read operation output by the magnetic reader 205.

The magnetic reader 205 may be embodied as an external magnetic reader in many forms including but not in any way limited to a patch, a necklace, belt, wrist band, arm band, leg band, or a handheld device. The magnetic reader 205 may perform a read operation by sending out a signal that is used to detect the bio-compatible magnetic pattern of nano-particles on at least part of a surface of the pill.

In an embodiment of the present disclosure, the magnetic reader 205 may include a permanent magnet. However, in some embodiments of the present disclosure, the magnetic reader may include an electromagnet. The magnetic reader 205 may be controlled by a microcontroller 220 that periodically controls the magnetic reader to perform the read operation.

The wearable device 200 shown in FIG. 2A is a patch worn near the waist, which may facilitate detecting magnetically coded patterns on one or more pills within the stomach of the patient. However, in some embodiments, the wearable device 200 may be a necklace having a magnetic reader and a wireless transceiver. The strength of the magnet for a necklace used to read magnetic patterns on pills within the stomach of a patient should be stronger than the strength of a magnet in a patch that is worn on the waist because of the difference in distance from the patient's stomach.

Figure 2B:
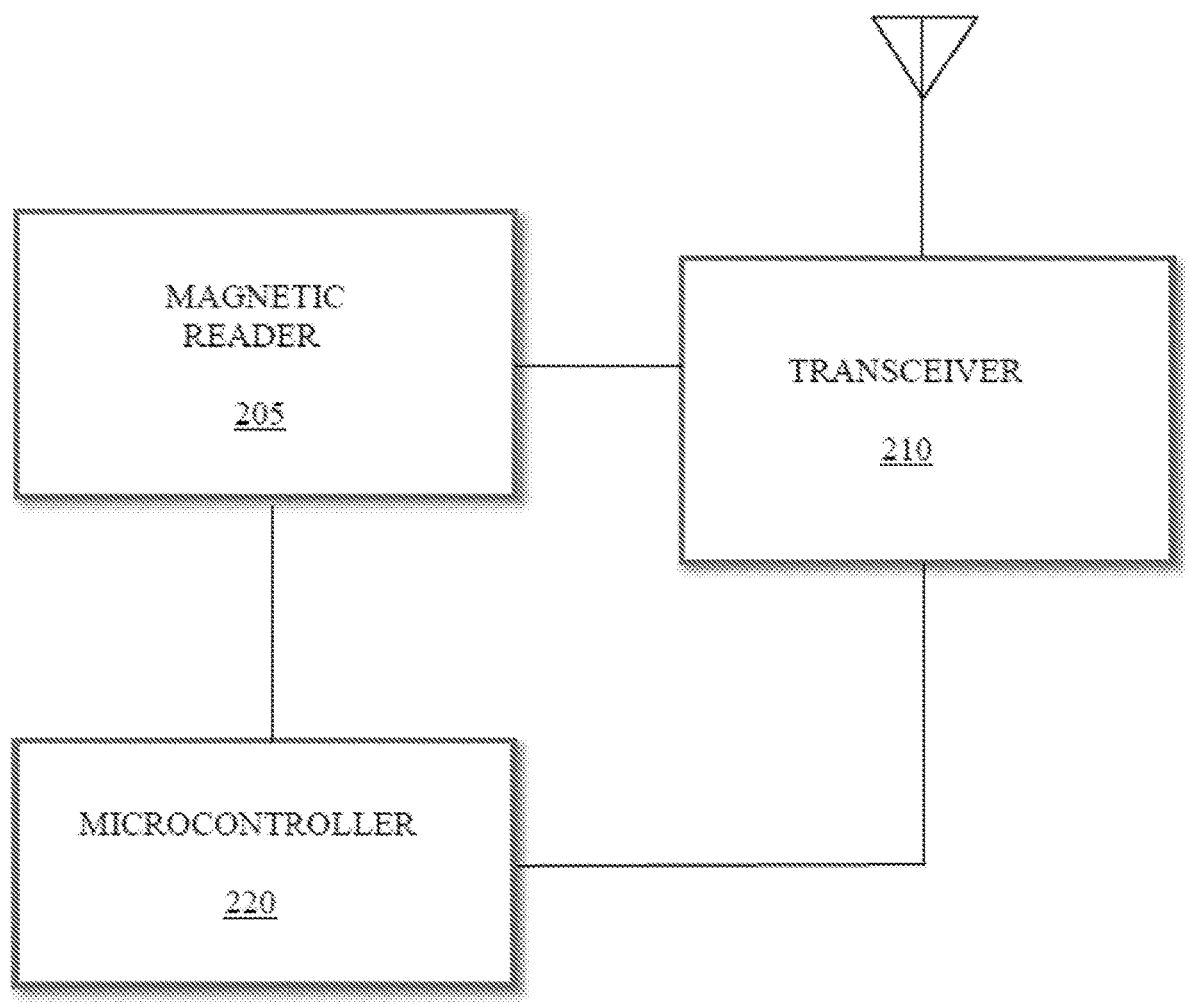
FIG. 2B is a schematic of a wearable device of a system for medication detection, consistent with an illustrative embodiment of the present disclosure.

In addition, the wearable device 200 may utilize two types of communication, based on magnetic and RF-based communications. For example, from inside the body to an external patch, a magnetic reader may be strong enough to read the magnetic pattern on at least one pill in the patient's body from a range of about 20 cm to 40 cm. However, when utilizing RF-based communications from the wearable device 200 to smart devices or the cloud, there may be a distance of about 25-30 feet between the wearable device 200 and the smart devices or the cloud. The wearable device may use, for example, WiFi to communicate with the smart device or the cloud. In some embodiments in which a smartphone or smartwatch communicates with the wearable device 205, the distance may be far less than the aforementioned 25-30 feet. Thus, Bluetooth, NFC, ZigBee, DECT or WiFi are some examples of communication protocols that may be used. As shown in FIG. 2B, the wearable device 200 may be operatively coupled to the wireless transceiver 210, and the wireless transceiver 210 may transmit the read result to one or more smart devices or to a device in the cloud.

In an embodiment of the present disclosure, if the magnetic reader 205 includes an electromagnet, the microcontroller 220 shown in FIG. 2B may be configured to perform the read operation multiple times until a threshold is reached (see FIG. 4B), or until there is a detection of a magnetic pattern within the body of the person. The time and number of read operations may be configured based on the types of medications taken by a person.

For example, the microcontroller 220 may control the magnetic reader 205 to perform a read operation in four-hour intervals if the prescribed medication is to be taken every four hours, or twelve-hour intervals if the prescribed medication is to be taken twice per day. Due to the inconsistency of some patients to take their prescribed medications at the proper interval, the microcontroller 220 may be configured to control the magnetic reader 205 to retry a read operation, for example, every half hour, quarter hour, every five minutes, or at some other predefined interval, because the patient may, for example, take the prescribed medication ten hours apart on one day instead of the recommended twelve hours.

Thus, performing read operations at periodic intervals may permit the wearable device 200 to detect that a patient took medication at a time that deviated from the schedule, e.g., the medication was taken too soon after the previous dose. Otherwise, the read operation at a scheduled interval could lead to a false result, namely that the person has not taken their prescribed medication, rather than detecting that the medication was taken earlier than scheduled. In the case of persons with cognitive problems, or multiple caretakers such as hospitals, nursing homes, the performing of read operations at periodic intervals may prevent the possibility that the person is given another dose of medication because the off-schedule dose was missed by the wearable device.

In an embodiment of the present disclosure, a system may track whether the wearable device 200 has indicated whether or not one or more pills 207 having a magnetic pattern have been detected within the patient's body. A reminder may be sent to the patient's smartphone, for example, if a predetermined period has passed and one or more pills prescribed to a patient have not been detected as being consumed.

Moreover, in an embodiment of the present disclosure, a designated nurse's station, doctor's office, etc., may be notified when the consumption of pills is off schedule, or not consumed at all. This information may also be stored for future patient monitoring. For example, a doctor can check whether a patient has been taking medication for diabetes as prescribed, which can facilitate the doctor in determining whether a particular blood sugar level may be based on inconsistent consumption of medication, rather than non-adherence to a prescribed diet. In some cases, such as taking blood thinners that prevent blood clots from forming in stents, or anti-rejection medication for organ transplant patients, the tracking of whether medication is being consumed as prescribed by detecting magnetic patterns encoded on the pills provides a way to enhance the delivery of healthcare.

In addition, the magnetic reader 205 may be operatively coupled to a storage device (not shown), such as a buffer or other type of memory. The storage device can store the results of one or more read operations performed by the magnetic reader 205.

The magnetically coated pill may have been coated with bio-compatible magnetic tags, which may include nano-particles sprayed by a magnetic tracking apparatus as discussed hereinabove. Alternatively, the pill may have been coated with nano-particles in a magnetic pattern at the point of manufacture. The pill bottle or container may have an integrated magnetic sensor that identifies the drug contained within. According to the type of drug and its dosage, different types of pills may have patterns with respectively different magnetic strengths and shapes with controlled multiple magnetic depositions according to the type of drug and the dosage. Thus, a patient who takes multiple pills for different conditions can be monitored as to whether all of the medications are being taken as prescribed. In addition, a reminder may be sent from the smartphone or network if the prescribed pills are not detected by the magnetic reader 205.

In addition, the doctor, pharmacy, or other healthcare provider may use cloud-based analytics to update the medicine usage information for a patient received from the external magnetic reader.

Figure 3:
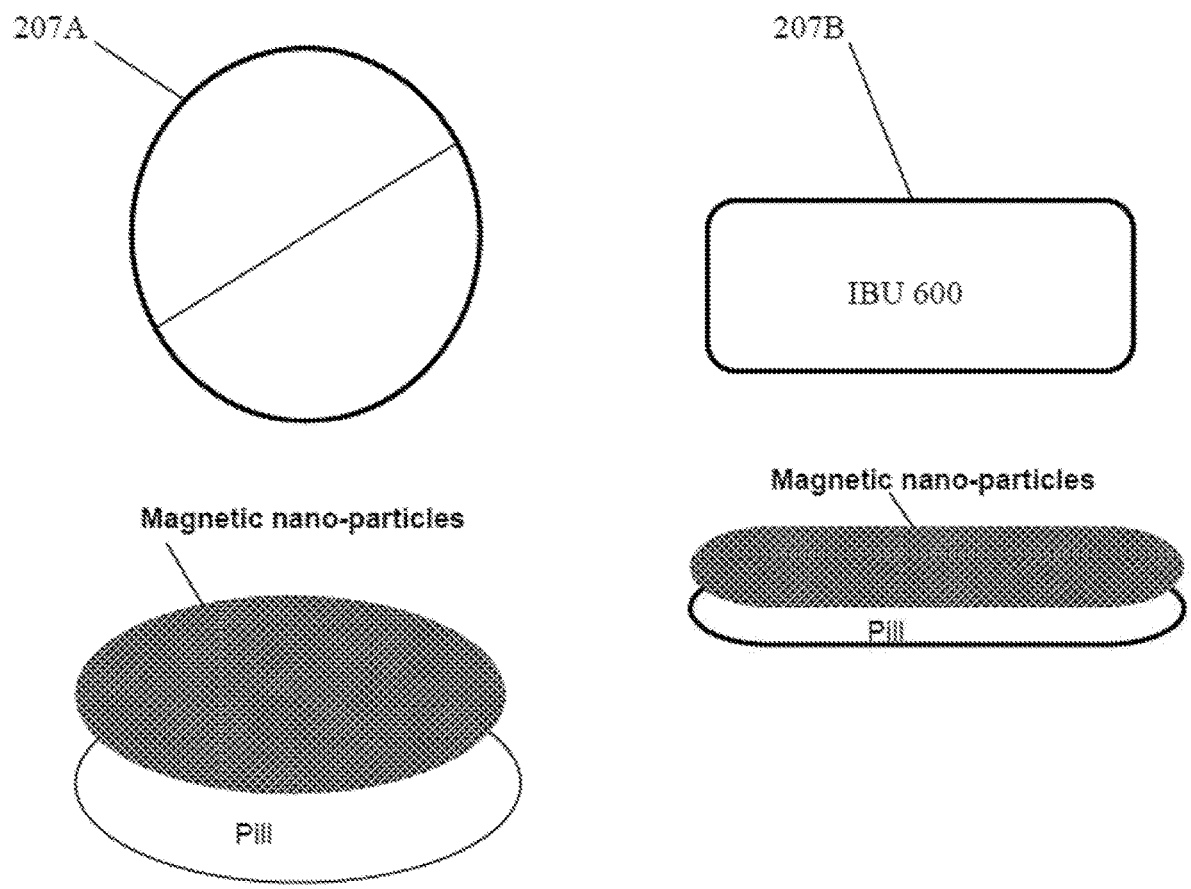
FIG. 3 is an example of a tablet and a capsule having a magnetic pattern coated thereon, consistent with an illustrative embodiment of the present disclosure.

FIG. 3 shows two types of pills that may be encoded with magnetic patterns. For example, there is a tablet 207*a* and a capsule 207*b*. In the case of the capsule, the imprint code can be clearly seen (IBU 600). The tablet may have the imprint code on the back side that is not shown.

With continued reference to FIG. 3, a magnetic nanoparticle coating is shown directly below the respective pill 207*a*, 207*b*. In various embodiments, the magnetic particles sprayed thereon may be, for example, a readable bar code, NDC number, hologram, logo, pharmaceutical company selected code, a combination of codes, an alpha-numeric code, etc. Thus, the magnetic patterns shown in FIG. 3 have been provided for illustrative purposes and do not limit the scope of the appended claims.

Figure 4A:
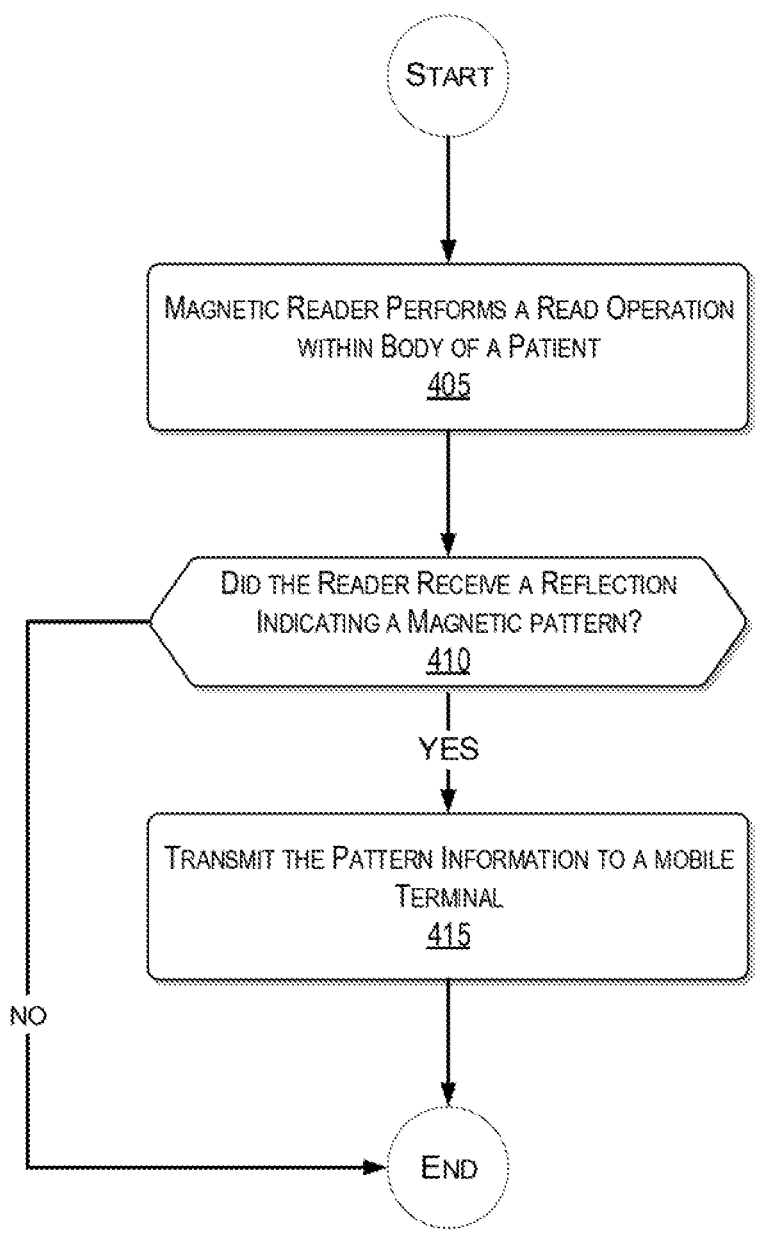
FIG. 4A is a flowchart illustrating an operation of a system for medication detection, consistent with an illustrative embodiment of the present disclosure.

FIG. 4A is a flowchart illustrating an operation of a system for medication detection, consistent with an illustrative embodiment of the present disclosure that will be discussed in more detail hereinbelow with additional reference to FIG. 2A.

At operation 405, an external magnetic reader performs a read operation within the body of the patient. While FIG. 2A shows a magnetic reader 205 in the form of a wearable patch. However, the magnetic reader 205 can take various forms, such as a necklace, a belt, an article of clothing having the magnetic reader thereon, etc. It will be understood that the aforementioned examples do not limit the how the magnetic reader 205 may be realized.

In addition, there is pill 207 shown in FIG. 2A of the stomach of a patient. If the pill has a magnetic pattern on it, which may have been arranged on the pill by a magnetic tracking apparatus such as shown in FIG. 1A, the magnetic reader 205 at operation 405 emits a magnetic field that will read the magnetic pattern that is reflected back to the magnetic reader 205.

At operation 410, if the reader receives a reflection from a magnetic pattern, then at operation 415 the pattern information may be sent via a wireless transceiver 210 to a smart device, such as a mobile terminal or smartwatch, or may be sent directly by wireless transceiver 210 via WiFi to a device connected via cloud computing. At operation 410, if the magnetic reader 205 does not receive read magnetic pattern, the operation may end. The smart device or device connected via cloud computing may be configured to determine that the lack of reception of pattern information from the wireless transceiver 210 is indicative that the patient has not taken their prescribed medication. A notice could be sent to the smart device, a nurse's station, or healthcare professional that the prescribed medication may not have been consumed. The patient's smart device can receive a reminder in the form of a text, email, alarm, or other type of notification.

Figure 4B:
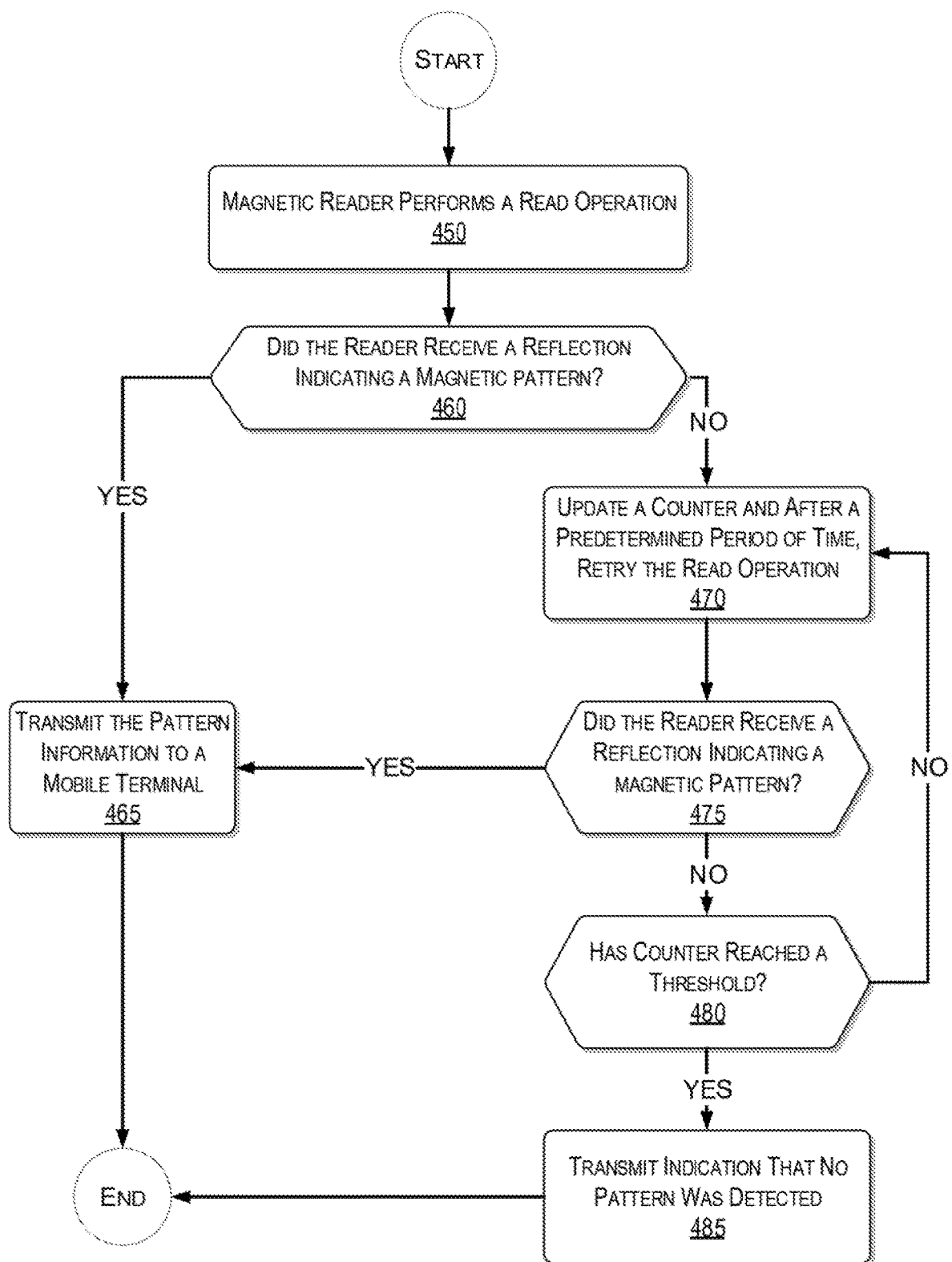
FIG. 4B is a flowchart illustrating an operation of a system for medication detection, consistent with an illustrative embodiment of the present disclosure.

FIG. 4B is a flowchart illustrating an operation of a system for medication detection, consistent with an illustrative embodiment of the present disclosure, that will be discussed in more detail hereinbelow with additional reference to FIG. 2A.

In the embodiment of the system for medication detection in FIG. 4B, a microcontroller 220 (see FIG. 2B) may be configured to control the operation of the magnetic reader 205. In this embodiment, the magnetic reader may include an electromagnet. Thus, the magnetic field may be projected periodically to read a magnetic pattern on the surface of a pill is in the patient's stomach. Patients may not always take their medication at the same time or times each day, and thus repetitive read operations may be made at least until a magnetic pattern is received from a read operation, or a settable threshold of retries is reached. Alternatively, when the magnetic reader 205 includes an electromagnet, read operations may be performed, for example, at 15-minute intervals without regard to a threshold of retries. It will be understood that the aforementioned example of a 15-minute interval is provided for explanatory purposes, and intervals longer, shorter, or varied in duration are all consistent with the present disclosure.

At operation 450, the magnetic reader performs a read operation. With reference to FIG. 2A, there is pill shown in the stomach of a patient. If the pill has a magnetic pattern on it, which may have been arranged on the pill by a magnetic tracking apparatus such as shown in FIG. 1A, the magnetic reader 205 at operation 405 emits a magnetic field that will read the magnetic pattern that is reflected back to the magnetic reader 205.

At operation 460, if the magnetic reader received a reflection from the magnetic pattern on a pill, then at operation 465, the pattern information may be transmitted to a smart device, such as a smartphone, smart watch, mobile terminal, by a transceiver 210, such as shown in FIG. 2B. The transceiver may wirelessly transmit the information to the smart device using, for example, Bluetooth, WiFi, NFC, DECT, ZigBee, etc. Alternatively, as previously discussed regarding FIG. 4A, the wireless transceiver 210 may transmit the pattern information to a device via the cloud. The device may be a server or other computing device configured to communicate with the microcontroller 220 (see FIG. 2B).

With continued reference to FIG. 4B, if at operation 460 the magnetic reader 205 did not receive a reflection of a magnetic pattern from a pill, at operation 470 the microcontroller may update a counter and control a retry of the read operation. The microcontroller may be configured to determine whether a predetermined time period has passed from the previous read operation before controlling the magnetic reader 205 to perform a retry.

At operation 475, if the reader received a reflection of a magnetic pattern read from a pill, then the microcontroller 220 may control the wireless transceiver 210 to transmit the pattern information to a smart device such as a smartphone, smart watch, mobile terminal, or other device connected via the cloud.

However, if at operation 475 the reader did not receive magnetic pattern information, at operation 480 the microcontroller 220 may check whether the counter has reached a threshold. If the value of the counter has not reached a threshold, then operation 470 will be performed again, wherein the counter is updated and a retry of a read operation is performed.

On the other hand, if at operation 480 the counter has reached a threshold, then the microcontroller 220 may be configured to control the wireless transceiver 210 to transmit an indication that no magnetic pattern has been detected.

In some embodiments of the present disclosure, the magnetic reader 205 may be operatively coupled to a transducer (not shown). Under control of the microcontroller 220, the transducer may vibrate or provide some type of audio, visual, or audio-visual indication as a reminder to the patient that there was no indication that they took their medication. The smart device in communication with the wireless transceiver 210 may be notified and may remind the patient via an alarm, and/or a display, text message, email, or other type of communication.

Computer Program Product

In still another embodiment of the disclosure, a computer program product may be realized as an application (e.g., an app) for a smart device such as a smartphone, smartwatch, mobile terminal or other device configured for operation with the system for a system for medication detection according to the present disclosure. The pill or pills may have a magnetic pattern thereon arranged by a magnetic tracking apparatus as discussed hereinabove, or may have been arranged on the pill by the manufacturer. The computer program product includes computer readable program instructions that may be provided to a processor of a computer, special purpose computer, smart device or other programmable data processing apparatus to produce a machine, such that the instructions execute via the processor of the computer, smart device or other programmable data processing apparatus.

Figure 5A:
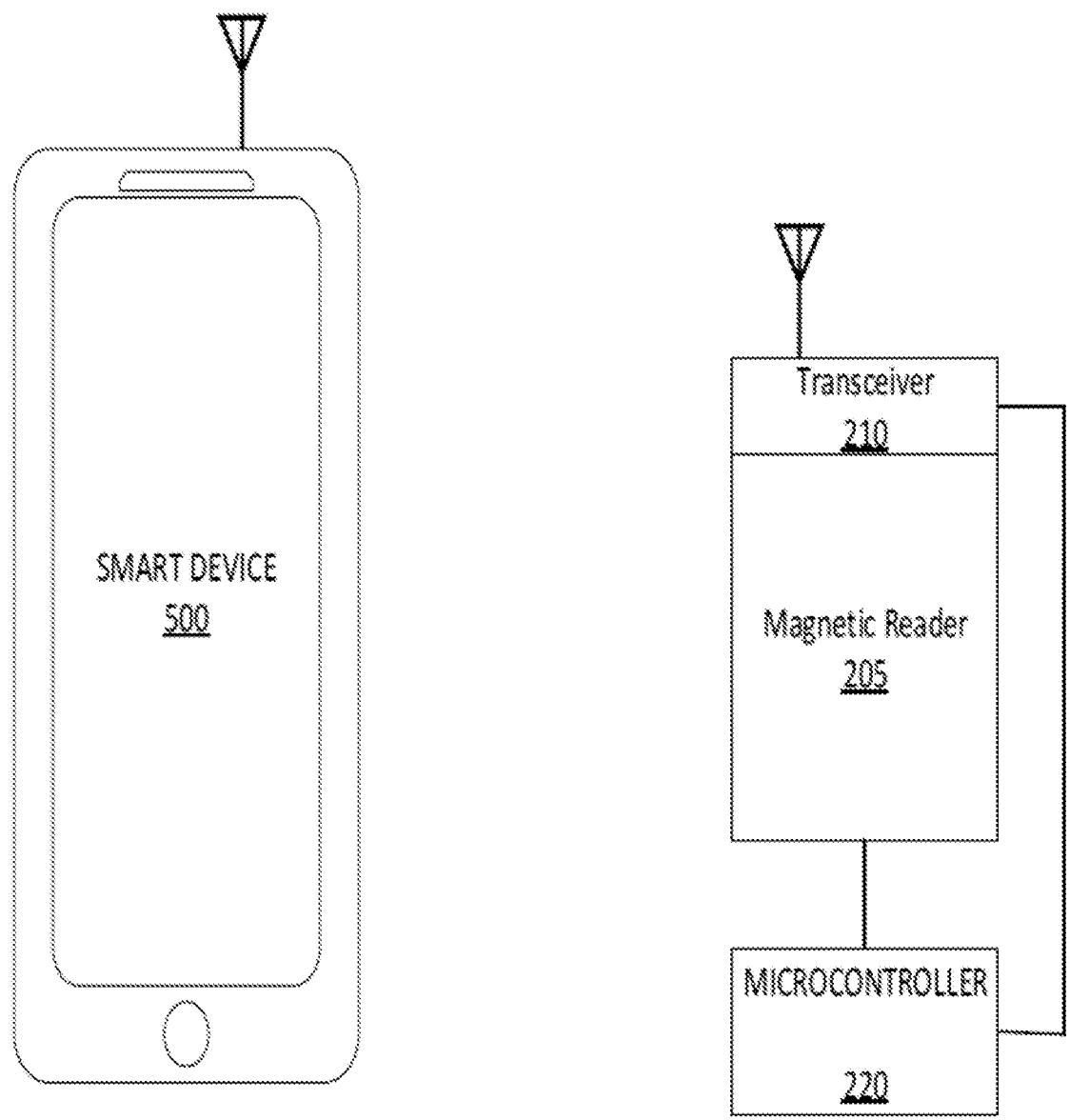
FIG. 5A illustrates one example of a smart device configured to control a system for medication detection according to some embodiments of the present disclosure.
Figure 5B:
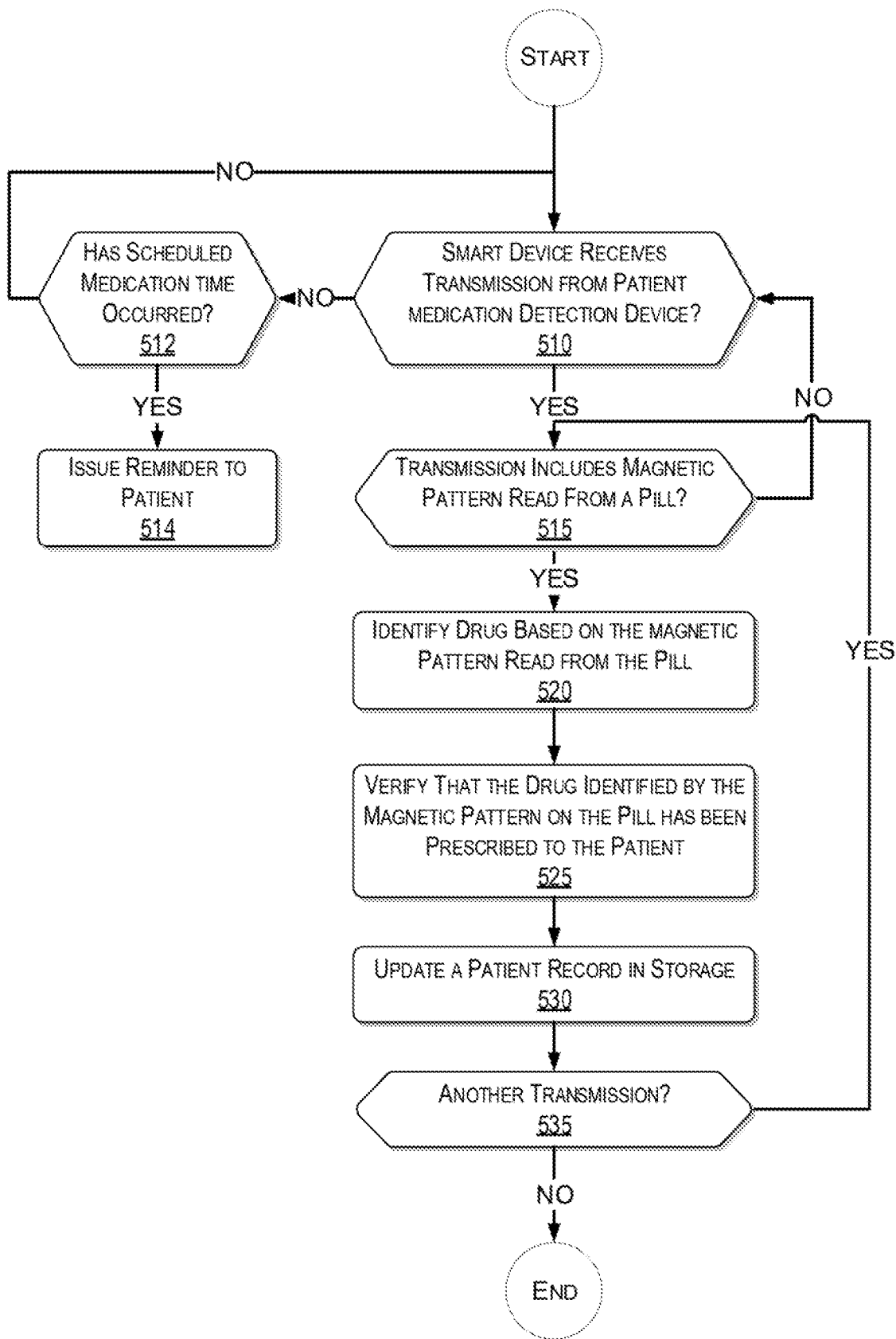
FIG. 5B is a flowchart illustrating an example of the operation of a computer program product when executed by a smart device according to some embodiments of the present disclosure.

FIG. 5A illustrates one example of a smart device 500 configured to control a patient medication detection apparatus according to some embodiments of the present disclosure, and FIG. 5B is a flowchart illustrating an example of the operation of a computer program product when executed by a device such as by a smart device shown in FIG. 5A. The computer program product may be executed by other types of computing devices, including but not limited to a smartwatch, a notebook, mobile terminal, etc.

With reference to FIG. 5A, a smart device 500 includes a wireless transceiver 210 that is coupled to a magnetic reader 205 of a patient's medication detection device. Such a detection device may be embodied as the magnetic reader 205, wireless transceiver 210, and microcontroller 220 shown in FIG. 2B. It will be understood that while a transceiver 210 is shown, the device may have only a transmitter, or a separate transmitter and receiver.

While the smart device 500 shown in FIG. 5A is a handheld device such as a smartphone or tablet, it will be understood that the smart device 500 may be realized in many forms that include a smartwatch or a mobile terminal. The smart device 500 includes at least one processor that when loaded with executable code according to some embodiments of the present disclosure, enables the smart device to interact with a patient medication detection device that may include the magnetic reader 205, wireless transceiver 210, and microcontroller 220 as shown. In the example of a smart device 500 such as a smartphone, the computer program product may be an app provided by the manufacturer or may be subsequently downloadable.

The patient medication detection device (205,210,220) shown in FIG. 5A may detect via the magnetic reader 205 whether a patient has consumed at least one pill with a magnetic pattern of bio-compatible magnetic nano-particles. The microcontroller 220 may be configured to control wireless transceiver 210 to transmit the information read by the magnetic reader 205 to the smart device 500.

The smart device 500 may include, or may be operatively coupled with, a memory having stored information regarding various magnetic patterns and the type and dose of a drug associated with each respective pattern. The smart device may optionally be configured to compare the identified magnetic pattern with a drug list of a specific patient to verify that the detected medication was prescribed to the patient. In some embodiments of the present disclosure, in a case where a particular patient's pills are coded with a customized magnetic pattern (e.g. a pattern dynamically selected by a pharmacy or health care facility such as a hospital), this information may be provided to the smart device 500 by a magnetic apparatus shown in FIG. 1A. In some embodiments of the present disclosure, the smart device includes a scanner such as a bar code scanner, the computer program product may configure the smart device to prompt for an input function in which the code on a pill bottle is scanned, providing the smart device with patient information, as well as the type and dosage of the medication. Accordingly, when the smart device 500 receives a transmission from a patient medication detection device, such as a wearable device, the smart device 500 can identify the type of drug and dosage based on the reading of the magnetic pattern on the pill by the magnetic reader 205. It will be understood that the aforementioned discussion of FIG. 5A is provided for illustrative purposes.

With continued reference to FIG. 5A, the smart device 500 may have access to a patient's drug schedule and may be configured to issue a notification if the wireless transmitter 210 does not transmit one or more expected magnetic patterns associated with a patient's drug schedule. The notification output may be a reminder/alarm that may be displayed by the smart device 500, or may be an audio or audio-visual alarm. The smart device 500 may also vibrate to provide notification about expected magnetic patterns not being detected by the magnetic reader 205. The smart device 500 may also be configured to notify a healthcare professional which may include a nurse's station in a hospital or nursing home that an expected dosage of medication for a particular patient may have been missed.

As previously discussed, a wearable magnetic reader 205 may include an actuator (not shown) and the smart device 500 may transmit a signal to the microcontroller to cause the actuator to vibrate, beep, flash, and/or any combination of warnings. If the patient is not directly monitored by a nurse or healthcare professional (e.g., the patient is at home) the actuator can remind the patient to take their prescribed medication. The smart device may display the medication that has been missed. In addition, a text, or email may also be sent to a designated patient advocate such as a family member regarding the missed medication.

With regard to the smart device 500, it will be understood that such devices may include a microprocessor or any suitable type of processing circuitry, such as one or more general-purpose processors (e.g., ARM-based processors), a Digital Signal Processor (DSP), a Programmable Logic Device (PLD), an Application-Specific Integrated Circuit (ASIC), configured for operation. Such smart devices include one or more transceivers for wireless communication in multiple protocols, such as, for example, WiFi, Bluetooth, and cellular. The smart device 500 may utilize other wireless protocols, including but not limited to NFC, ZigBee, or DECT.

FIG. 5B is a flowchart illustrating an example of the operation of a computer program product when executed by the processor of a computer device. While FIG. 5A shows a smart device 500, the inventive concept is not limited to the smart device shown in FIG. 5A.

At operation 510, it is determined whether the smart device 500 receives a communication from a patient's medication detection device, which may include but is not limited to the device shown in FIG. 2B. The smart device 500 receives a communication transmitted by the wireless transceiver 210. If the smart device 500 did not receive a transmission from the patient medication detection device, it is determined at operation 512 whether the scheduled medication time for a particular patient has occurred. If the scheduled medication time has occurred and there was no transmission received from the patient medication detection device, at operation 514 the patient is issued a reminder. The reminder may be in the form of a display on the smart device, that may flash, and/or an audible tone, a vibration, or any combination of warnings. The smart device 500 may also issue a notification to a nurse or healthcare provider.

At operation 515, the smart device 500 determines whether the transmission received at operation 510 included magnetic pattern information read from a pill. If the information is identified as including magnetic pattern information, then at operation 520, the drug and optionally the dosage may be identified by the smart device 500. For example, the smart device 500 may have stored information regarding a plurality of magnetic patterns and their associated types of medications. Alternatively, the smart device may communicate with a server or cloud-based device to obtain identification of the magnetic pattern information received from the magnetic reader 205 via the wireless transceiver 210.

Optionally, at operation 525, the smart device 500 may perform a safety check by comparing the drug identified by the magnetic pattern against a list of drugs that have been prescribed to the particular patient. At operation 530, the smart device may update the patient's list or may notify the health care provider to confirm that the drug identified by the magnetic pattern was in fact prescribed to the patient. In addition, when a drug identified by the magnetic pattern is on the list of medications for the patient, the smart device 500 may also update a patient's daily record of drugs consumed. Accordingly, the smart device 500, and the healthcare provider may be able to check whether a patient has been taking their medication as prescribed. This feature can assist a healthcare provider in determining whether the particular medications are working as expected, or whether certain patient symptoms may be a result of the patient failing to take the medications as prescribed.

At operation 535, if another transmission is received by the smart device 500, the process may again perform operation 515 to determine whether the information transmitted includes a magnetic pattern read from another pill. The smart device 500 would then continue to execute the program indicated in the flowchart as discussed hereinabove.

CONCLUSION

The descriptions of the various embodiments of the present teachings have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

While the foregoing has described what are considered to be the best state and/or other examples, it is understood that various modifications may be made therein and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

The components, steps, features, objects, benefits and advantages that have been discussed herein are merely illustrative. None of them, nor the discussions relating to them, are intended to limit the scope of protection. While various advantages have been discussed herein, it will be understood that not all embodiments necessarily include all advantages. Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain.

Numerous other embodiments are also contemplated. These include embodiments that have fewer, additional, and/or different components, steps, features, objects, benefits and advantages. These also include embodiments in which the components and/or steps are arranged and/or ordered differently.

The present application may be a system, a method, and/or a computer program product. The computer program product may include a computer-readable storage medium (or media) having computer readable program instructions thereon for causing a processor to carry out aspects of the present application.

The computer-readable storage medium can be a tangible device that can retain and store instructions for use by an instruction execution device. The computer-readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer-readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present application may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present application.

Aspects of the present disclosure are described herein with reference to call flow illustrations and/or block diagrams of a method, apparatus (systems), and computer program products according to embodiments of the present disclosure. It will be understood that each step of the flowchart illustrations and/or block diagrams, and combinations of blocks in the call flow illustrations and/or block diagrams, can be implemented by computer readable program instructions.

These computer readable program instructions may be provided to a processor of a computer, special purpose computer, or other programmable data processing apparatus to produce a machine, such that the instructions, which execute via the processor of the computer or other programmable data processing apparatus, create means for implementing the functions/acts specified in the call flow process and/or block diagram block or blocks. These computer readable program instructions may also be stored in a computer-readable storage medium that can direct a computer, a programmable data processing apparatus, and/or other devices to function in a particular manner, such that the computer readable storage medium having instructions stored therein comprises an article of manufacture including instructions which implement aspects of the function/act specified in the call flow and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the call flow process and/or block diagram block or blocks.

The flowchart and block diagrams in the Figures illustrate the architecture, functionality, and operation of possible implementations of systems, methods, and computer program products according to various embodiments of the present disclosure. In this regard, each block in the call flow process or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or call flow illustration, and combinations of blocks in the block diagrams and/or call flow illustration, can be implemented by special purpose hardware-based systems that perform the specified functions or acts or carry out combinations of special purpose hardware and computer instructions.

While the foregoing has been described in conjunction with exemplary embodiments, it is understood that the term "exemplary" is merely meant as an example, rather than the best or optimal. Except as stated immediately above, nothing that has been stated or illustrated is intended or should be interpreted to cause a dedication of any component, step, feature, object, benefit, advantage, or equivalent to the public, regardless of whether it is or is not recited in the claims.

It will be understood that the terms and expressions used herein have the ordinary meaning as is accorded to such terms and expressions with respect to their corresponding respective areas of inquiry and study except where specific meanings have otherwise been set forth herein. Relational terms such as first and second and the like may be used solely to distinguish one entity or action from another without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "a" or "an" does not, without further constraints, preclude the existence of additional identical elements in the process, method, article, or apparatus that comprises the element.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various embodiments for the purpose of streamlining the disclosure. This method of disclosure is not to be interpreted as reflecting an intention that the claimed embodiments have more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separately claimed subject matter.

What is claimed is:

1. A magnetic tracking apparatus comprising:
   a pill feeder having an inlet, an outlet, and a first valve configured to control an opening and a closing of the outlet of the pill feeder;
   a chamber arranged in communication with the outlet of the pill feeder to receive a pill;
   a microcontroller configured to control operation of the first valve; and
   a magnetic nano-particle applicator controlled by the microcontroller to deposit bio-compatible nano-magnetic particles in a magnetic pattern onto a surface of the pill within the chamber.

2. The magnetic tracking apparatus of claim 1, further comprising a wireless communication system operatively coupled to the microcontroller to monitor a condition of the pill feeder, the chamber, the magnetic nano-particle applicator and the outlet.

3. The magnetic tracking apparatus according to claim 1, wherein the magnetic nano-particle applicator comprises of one a sprayer or an inkjet printer.

4. The magnetic tracking apparatus according to claim 1, wherein the magnetic nano-particle applicator is configured to deposit the bio-compatible nano-magnetic particles by stencil printing.

5. The magnetic tracking apparatus of claim 2, further comprising:
- a pill conduit forming a passageway in communication with the chamber; and
- a pill collector substantially aligned with the pill conduit to receive the pill having the magnetic pattern, wherein the chamber includes a second valve having a closed position that retains the pill within the chamber, and in an open position in communication with the passageway for the pill to exit the chamber, wherein the wireless communication system communicates with a smart device.

6. The magnetic tracking apparatus of claim 5, wherein the pill collector comprises a pill bottle including an integrated magnetic sensor.

7. The magnetic tracking apparatus according to claim 5, wherein the microcontroller is configured to control the opening and the closing of the first valve and the second valve at a substantially constant rate.

8. The magnetic tracking apparatus according to claim 1, wherein the magnetic pattern has a magnetic strength and a shape based on a shape of the pill.

9. The magnetic tracking apparatus according to claim 1, further comprising an input reader configured to read information from a label associated with the pill to be tracked, wherein the input reader transmits the read information to a memory operatively coupled to the microcontroller.

10. The magnetic tracking apparatus of claim 1, further comprising an input reader configured to read at least an imprint code on the pill,
- wherein the input reader is configured to transmit the imprint code to a memory operatively coupled to the microcontroller, and
- wherein the microcontroller controls the magnetic nano-particle applicator to spray the magnetic pattern onto at least a portion of the pill based on the imprint code on the pill.

11. The magnetic tracking apparatus of claim 10, further comprising a sensor configured to detect one or more of a shape, a size information, and a color of the pill in the pill feeder.

12. The magnetic tracking apparatus of claim 1, wherein the microcontroller controls the magnetic nano-particle applicator to deposit a magnetic pattern that identifies a type of drug and a dosage of least one substance included in the pill.

13. A method for identifying and tracking pills, the method comprising:
- reading, by an input reader, information associated with a pill to be tracked;
- opening, under control of a microcontroller, a first valve configured to control an opening and a closing of an outlet of a pill feeder;
- depositing, under control of the microcontroller, a magnetic pattern of nano-particles onto a surface of the pill within a chamber arranged in communication with the outlet of the pill feeder in which the chamber includes a second valve having a closed position that retains the pill within the chamber, and in an open position communicates with a passageway for the pill to exit the chamber; and
- receiving, by a pill collector, the pill having the magnetic pattern sprayed thereon,
- wherein the microcontroller is configured to control operation of the input reader, the first valve and the second value, and the depositing of the magnetic pattern of nano-particles via a wireless communication system.

14. The method according to claim 13, wherein the depositing of the magnetic pattern of nano-particles is performed by a sprayer that is configurable by the microcontroller in real time.

15. The method according to claim 13, wherein the depositing of the magnetic pattern of nano-particles is performed by an inkjet printer.

16. The method according to claim 13, wherein the depositing of the magnetic pattern of nano-particles is performed by stencil printing.

17. The method according to claim 13, wherein the reading of information by the input reader comprises at least one of (i) reading an imprint code on the pill to be tracked or comprises reading a label associated with the pill to be tracked.

18. The method according to claim 13, wherein the reading of information by the input reader comprises reading a label having a National Drug Code (NDC) number associated with the pill to be tracked.

19. The method according to claim 13, wherein the reading of information by the input reader comprises scanning one or more of a shape, size, or color of the pill to be tracked.

20. A pill having a readable magnetic pattern arranged on its surface according to the method of claim 13.

* * * * *